United States Patent [19]
McKelvey et al.

[11] Patent Number: 5,088,316
[45] Date of Patent: Feb. 18, 1992

[54] APPARATUS AND METHOD FOR TESTING MATERIAL SAMPLES FOR GAS DIFFUSION CHARACTERISTICS

[75] Inventors: William F. McKelvey, Langhorne, Pa.; Jay W. Davis, Clifton, Colo.

[73] Assignee: Versar, Inc., Springfield, Va.

[21] Appl. No.: 413,198

[22] Filed: Sep. 27, 1989

[51] Int. Cl.⁵ ............................................. G01N 15/08
[52] U.S. Cl. ......................................... 73/38; 73/865.6
[58] Field of Search .................................. 73/38, 865.6

[56] References Cited

U.S. PATENT DOCUMENTS

| | | |
|---|---|---|
| 2,310,111 | 2/1943 | Nordlander ............................. 73/38 |
| 3,285,699 | 11/1966 | Dulski et al. |
| 3,355,250 | 11/1967 | Gorring |
| 4,468,951 | 9/1984 | Garcia et al. ............................ 73/38 |
| 4,538,460 | 9/1985 | Schettler, Jr. ....................... 73/432 R |
| 4,602,503 | 7/1986 | Hile et al. ............................ 73/865.6 |
| 4,656,865 | 4/1987 | Callan ..................................... 73/38 |
| 4,791,822 | 12/1988 | Penny .................................. 73/865.6 |

FOREIGN PATENT DOCUMENTS

| | | | |
|---|---|---|---|
| 1168469 | 6/1984 | Canada ..................................... 73/38 |
| 2310255 | 11/1973 | Fed. Rep. of Germany .......... 73/38 |
| 3641821 | 6/1988 | Fed. Rep. of Germany .......... 73/38 |
| 794411 | 1/1981 | U.S.S.R. ................................. 73/38 |
| 1150522 | 4/1985 | U.S.S.R. ................................. 73/38 |
| 1291851 | 2/1987 | U.S.S.R. ................................. 73/38 |

*Primary Examiner*—Hezron E. Williams
*Assistant Examiner*—Joseph W. Roskos
*Attorney, Agent, or Firm*—Bacon & Thomas

[57] ABSTRACT

A method and apparatus for testing the gas diffusion characteristics of material samples includes a sealed test chamber in which one or more test cells are placed. A material sample is mounted on one end of a substantially cylindrical test cell. The chamber is then charged to a predetermined pressure and concentration of a test gas, such as radon. Periodically, gas samples are drawn through the other end of the test cell for analysis of test gas concentration, which indicates the capability of the material sample to diffuse, or prevent diffusion of, the test gas. For each test, a desired pressure differential is maintained across the material sample, and also between the chamber interior and ambient.

15 Claims, 2 Drawing Sheets

APPARATUS AND METHOD FOR TESTING MATERIAL SAMPLES FOR GAS DIFFUSION CHARACTERISTICS

BACKGROUND OF THE INVENTION

1. Field of the Invention

The present invention relates generally to gas diffusion testing of materials, and, more particularly, to closed system testing of materials for their permeability to specific gases.

1. Description of the Related Art

The prior art has long recognized the need for a system capable of testing building or other materials for their ability to prevent or allow diffusion of undesirable or desirable gases, respectively.

One prior art system for testing the capability of structural materials to prevent diffusion of radon gas is the "bucket test", which entails the use of two five-gallon buckets placed end to end. The opposed ends of the buckets are structured to remain open to each other save for the material to be tested, which is placed between the two openings so that gas passing from one bucket to the other necessarily diffuses across the test material. A radon source placed in the first, or "hot", bucket, provides the radon gas whose presence sensed in the second, or "cold", bucket, when compared to the hot bucket gas concentration, indicates the capacity of the test material to prevent diffusion of the radon gas. Such testing has been carried out at atmospheric pressure, with no direct control over the concentration of radon in the hot bucket.

A gas commonly found in inhabited areas, yet undesirable there, is radon gas. Radon is a radioactive elemental product of certain materials often found in the earth's crust. Due to its nature as a pressure-driven gas, it finds its way into buildings under the influence of pressure differentials present across the building structure. In particular, a "sealed" building, such as one closed for heating in winter or for cooling in summer, is susceptible to radon diffusion when external pressure changes cause differentials that cannot equilibrate quickly. A system for accurately testing a material sample for its diffusion characteristics under the influence of a pressure-driven gas, under conditions similar to actual use conditions, would give more useful information with respect to predicting in situ performance of the material.

SUMMARY OF THE INVENTION

The present invention improves upon the basic concept of the prior art bucket system by providing a sealed test chamber enclosing at least one test cell. The test cell has one open end for sealingly mounting a test sample, and a closed end having three ports. The supply and return ports enable circulation of diffused gas present in the test cell through the use of a pump located externally to the test chamber. A sample counter included as part of the recirculating system provides an indication of the amount of gas that has diffused across the test sample. The third port is a pressure sensing port, from which a manometer located externally to the test chamber determines relative pressure between the test cell and the test chamber.

The test chamber itself is charged with test gas from a test gas source also located externally to the test chamber. A series of tubes connects the test gas source to the test chamber, enabling an in-line pump to continually provide test gas to the chamber. A second manometer indicates relative pressure differential between the test chamber and ambient, so that the test gas supply can be monitored and regulated in both pressure and concentration.

The invention also lies in the testing method, which includes the maintenance of a specified pressure differential across the test sample to decrease the randomness of interaction between the test gas molecules and the test sample, as well as to provide diffusion characteristics of the test sample under conditions similar to those experienced in a normal application. In this manner, the diffusion characteristics of the test sample for the test gas can be determined for controlled parameters.

DETAILED DESCRIPTION OF THE PREFERRED EMBODIMENTS

Figure 1:
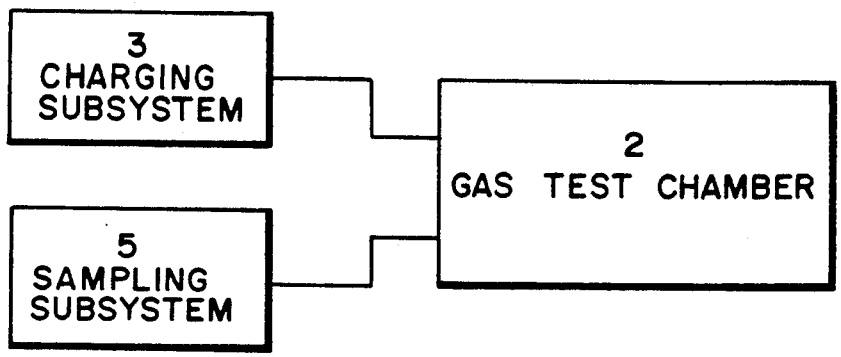
FIG. 1 shows a block diagram that generally depicts the relationship of the charging and sampling systems to the test chamber.
Figure 2A:
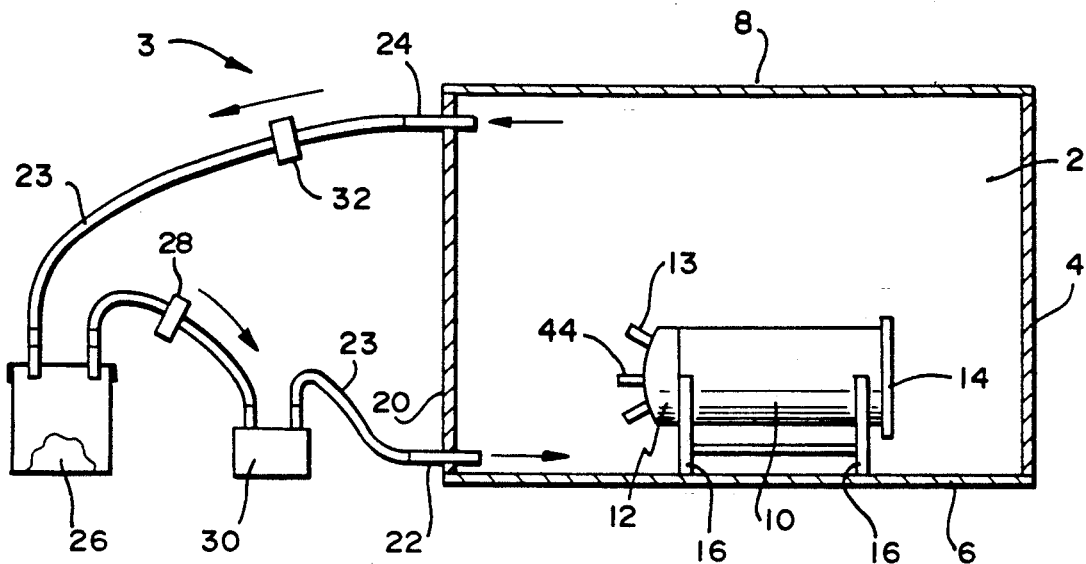
FIG. 2a details a side view of the charging system of the invention.
Figure 2B:
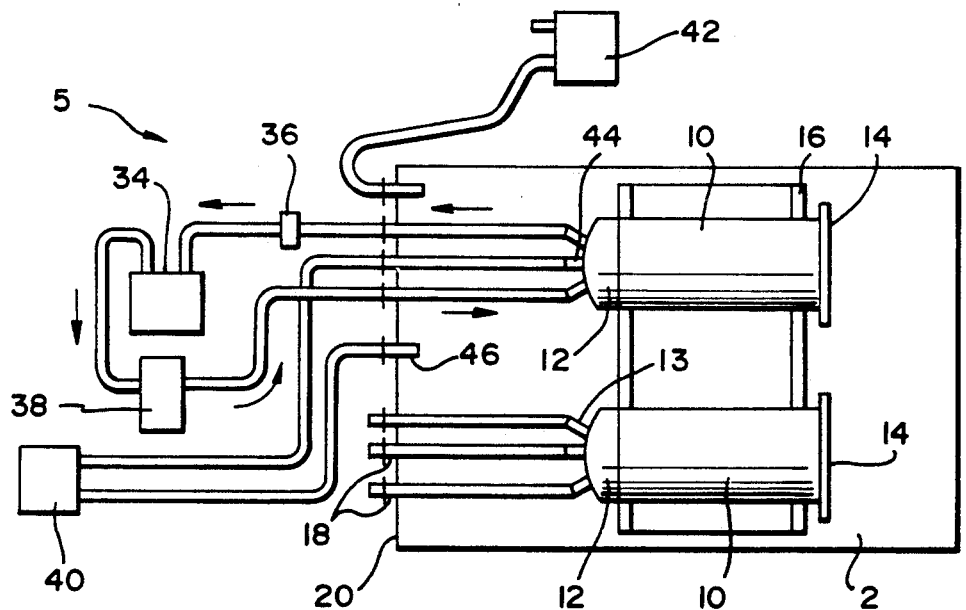
FIG. 2b details a top view of the sampling system of the invention.

FIG. 1 shows a schematic of a preferred embodiment of gas test chamber 2 along with charging subsystem 3 and sampling subsystem 5. FIGS. 2a and 2b detail the charging and sampling subsystems, and are shown separately for clarity.

Turning to FIG. 2a, gas test chamber 2 preferably comprises four rectangular walls 4 over rectangular base 6, although other shapes may be utilized for the chamber. The top 8 of test chamber 2 is removable for access to the interior of the chamber.

A test cell 10 is provided for each test to be carried out. As will be described in more detail below, the system is capable of testing more than one material at a time. Each test cell 10 preferably comprises a body that is impervious to the test gas, and capable of being sealed to external pressure save for an opening over which a test sample material is mounted. Further openings are provided for sampling and recirculating test gas that has permeated across the test sample, as described in more detail below.

In the embodiment shown, each test cell 10 is sealed at one end with an end cap 12, for example, made of the same material as the cell body, and each end cap 12 is preferably equipped with three nipples 13, which are connected to appropriate chamber ports 18 in one wall 20 of test chamber 2. Test sample 14 is mounted over an opening provided in test cell 10 opposite from end cap 12 using a releasable sealing compound.

Figure 3:
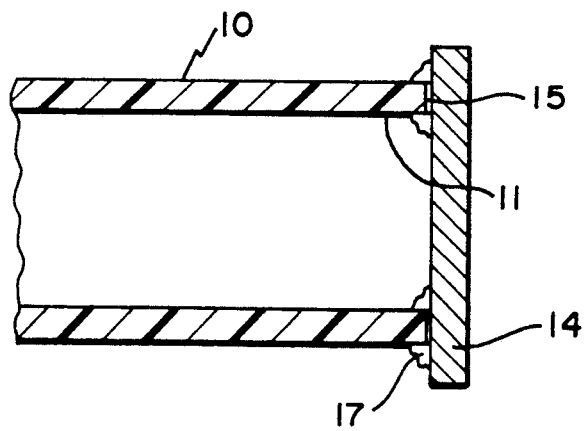
FIG. 3 is an enlarged vertical section view of the sample mounting end of a test cell.

By way of example, test cell 10 may comprise a cylindrical body having an open end 11, as shown, wherein the body is sufficiently thick to provide a lip surface 15 at the open end upon which test sample 14 can be mounted by using an adhesive sealant 17. (See FIG. 3). In a tested prototype, a ¼inch, (0.64 cm) thick cylinder provided a sufficient lip surface 15 to support an adhesive sealant for releasably bonding test sample 14 to test cell 10.

Any other means within the skill of the art could be used for mounting the sample 14 on the end of the cell 10; for example, an apertured backing plate (not shown) could be mounted over the open end 11 of the cell and the test sample 14 mounted on it, or the test cell 10 could be provided with a flanged end to provide a broader mounting surface for the sample 14. A sample could also be provided large enough to wrap over at least a portion of the end 11 of the test cell body 10 and bonded thereto. A threaded sample-supporting cap has been tested, but found lacking in seal integrity in comparison to the preferred mounting arrangement shown in the figures. However, if proper sealing could be established, this arrangement also could be used.

Each test cell 10 is supported within test chamber 2 by rack 16. Rack 16 may be designed to support any number of test cells 10.

In preferred form, a plurality of chamber ports 18 are provided in wall 20 of chamber 2. As shown in FIG. 2a, the charging system utilizes two of these ports, supply port 22 and return port 24, to maintain a predetermined pressure and concentration of test gas in chamber 2. Tubing 23 connects a source of test gas 26 to supply port 22 via in-line filter 28 and pump 30 to provide test gas to test chamber 2, while tubing 23 also connects return port 24 to the return side of test gas source 26 via another inline filter 32.

Turning to the top view of FIG. 2b, the sampling system shown performs two functions. First, the concentration of test gas that diffuses from chamber 2 into test cell 10 across test sample 14 is sensed and counted by sampling counter 34. Second, a circuit established from test cell 10 through one port 18 to sampling counter 34 via in-line filter 36, and back to test cell 10 via pump 38 provides continuous gas changes in test cell 10. Note that test cells 10 are shown rotated 90° so that the circulating system is clear in this top view.

FIG. 2b also illustrates how the system maintains a desired pressure differential across test sample 14. Manometer 40 displays the pressure differential sensed between test cell pressure sensing port 44 and chamber pressure sensing port 46. Similarly, chamber-ambient manometer 42 indicates the pressure differential between test chamber 2 and ambient pressure so that a desired pressure greater than atmospheric is maintained in test chamber 2 by pumping air into test chamber using, for example, pump 30.

In preferred preparation for a test, foreign particles should first be cleaned from the mounting surface of test cell 10. The mounting surface should also be trued, if necessary, to ensure that test sample 14 remains sealed to test cell 10 throughout a test. A releasable sealing compound such as a silicone gel is preferred to mount the test sample.

Once sample 14 is mounted, the seal is tested by applying a 1-inch/Hg "vacuum" to test cell 10 for five minutes. If a vacuum seal is not held for the entire five minutes, sample 14 must be resealed. The actual "vacuum" applied will vary with the type of material tested; a relatively delicate material, for example, will collapse under a sealant test pressure that would be appropriate for a more rigid material. So long as the seal integrity can be properly evaluated, the appropriate vacuum need not be rigidly defined.

Figure 4:
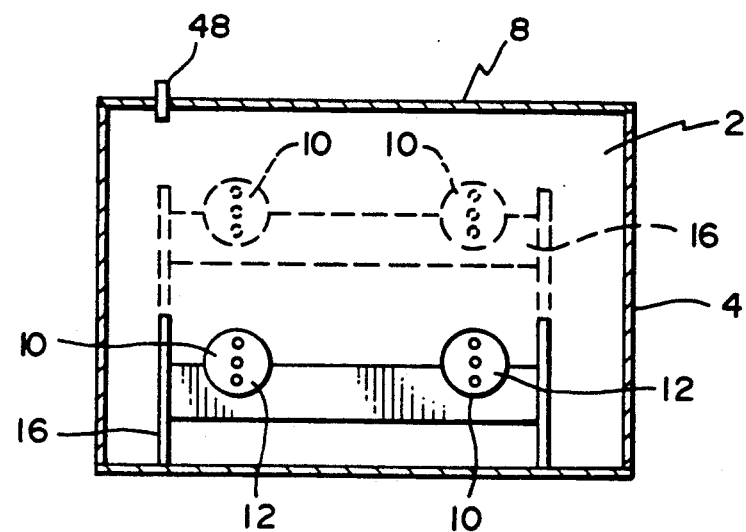
FIG. 4 is a front view taken of the test chamber.

Next, the properly prepared test cell 10 is placed on rack 16. As shown by broken lines in FIG. 4, more than one test cell 10 may be mounted for each testing process, and, preferably, one control cell is included for calibration purposes.

Once all test samples 14 have been properly mounted on test cells 10 and placed within test chamber 2, chamber lid 8 is replaced on test chamber 2. Before doing so, a gasket (not shown) is preferably applied along with an appropriate vacuum grease seal so that a desired pressure greater than atmospheric may be maintained within the chamber, thus maintaining a controlled pressure differential across each test sample 14. A plurality of bolts (not shown) disposed about the perimeter of lid 8 are then tightened down.

Once the tubes, filters and charging pump are hooked up for the charging system, the chamber is filled from source 26 with the desired test gas to a predetermined pressure and concentration, which pressure is sensed using manometer 42, and which concentration is sensed via test port 48. Manometer 40 may be used to verify that the pressure differential between test chamber 2 and the interior of each test cell 10 is approximately 0.1 in./H$_2$O (about 0.025 kPa), in a preferred example. The sampling system is then hooked up.

For radon gas diffusion testing, material samples are preferably tested for 4-24 hour test periods, with an increase of 0.1 in./H$_2$O (0.025 kPa) pressure differential across the test sample after each test period, and with a maximum recommended pressure differential between chamber 2 and ambient of approximately 10.5 in./H$_2$O (2.6 kPa). This corresponds to a differential pressure between chamber 2 and test cell 10 of approximately 6.5 in./H$_2$O (1.6 kPa), depending upon porosity of sample under test. Pressure control, as well as concentration control, may be manual as described above, or may be governed by an automatic system within the level of one skilled in the art.

In a preferred, although merely illustrative, embodiment of the invention, gas test chamber 2 is constructed of ½ inch thick (1.25 cm) clear acrylic, with an internal volume of 12 cubic feet (339.97 liters). Each test cell 10 is a circular cylinder of nominal 4-or 6-inch diameter PVC, Schedule 40 pipe having an internal volume of 0.102 cubic feet (2.89 liters) or 0.196 cubic feet (5.55 liters), respectively. All tubing 23 in the apparatus, both inside and outside test chamber 2, is commercially available latex tubing. Plastic or copper tubing, for example, could be substituted or additionally used, but latex tubing has the advantage of greater flexibility.

Test sample 14 itself may comprise a flexible membrane, preferably 6 inches (15.24 cm) square (or in diameter, if round), but in any case, large enough to be securely mounted. Rigid samples comprising cementitious coatings that are rigid after curing are preferably at least 7 inches (17.78 cm) square or 7 inches (17.78 cm) in diameter, if round. Of course, the sample thickness should be equal to that for a normal field application, although samples may be reinforced with a material that will not interfere with diffusion of the test gas. Thin films and membranes, in particular, should be so treated. Paints, for example, have been tested by application to a commercially-available filter paper.

Although the system described above has been especially designed and tested for use with radon gas, one skilled in the art will readily ascertain that other gases whose diffusion characteristics across certain materials is important may be employed. Furthermore, the invention may be applied to test for both the ability of a material to prevent gas diffusion as well as the ability of a material to allow diffusion of a desirable gas.

Various modifications of the invention disclosed in the foregoing description will become apparent to those skilled in the art. All such modifications that basically rely upon the teachings through which the invention has advanced the art are properly considered within the spirit and scope of the invention.

I claim:

1. A system for testing the gas diffusion characteristics of a test sample, comprising:
   a test chamber containing a test gas at a pressure greater than atmospheric;
   a test cell within said test chamber, and having an opening, and arranged to support a test sample over said opening, wherein said test cell and test chamber are arranged so that gas present in said test chamber may enter said test cell only by diffusing across said test sample through said opening; and
   counting means connected to said test cell for determining the concentration of test gas that diffuses across said test sample into said test cell.

2. A system for testing the gas diffusion characteristics of a test sample, comprising:
   a test chamber having at least one wall defining a chamber interior and a chamber exterior, said test chamber including a plurality of chamber ports for allowing the passage of gas between the interior and exterior of the chamber;
   a test gas source;
   means for charging the interior of the test chamber to a predetermined pressure and concentration of the test gas via the chamber ports;
   at least one test cell located inside the test chamber, each said test cell having at least one wall defining a test cell interior and a test cell exterior, said test cell including a plurality of cell ports for allowing the passage of gas between the interior and exterior of the test cell, and an opening arranged to support a test sample such that test gas in the test chamber may only enter the test cell interior by diffusing across the test sample;
   counting means for determining the concentration of test gas diffusing from the chamber interior to the test cell interior through the test sample; and
   means for circulating test gas between the test cell and counting means.

3. A gas diffusion test system as claimed in claim 2, wherein said charging means is arranged to charge the interior of the test chamber to a pressure greater than atmospheric.

4. A gas diffusion test system as claimed in claim 2, further comprising means for maintaining a substantially constant pressure differential between the test chamber and the test cell.

5. A gas diffusion test system as claimed in claim 2, wherein said test gas source is a source of radon gas.

6. A gas diffusion test system as claimed in claim 2, wherein said charging means comprises pump means for conveying the test gas in a circuit including the test gas source and the test chamber.

7. A gas diffusion test system as claimed in claim 6, wherein said charging means further comprises an in-line filter for removing undesirable elements from the test gas circulating in said circuit comprising the test chamber and the test gas source.

8. A gas diffusion test system as claimed in claim 2, further comprising means for maintaining a substantially constant pressure differential between the test chamber and ambient.

9. A gas diffusion test system as claimed in claim 2, wherein one of said test cells is a reference control cell including a test sample having known gas diffusion characteristics.

10. A gas diffusion test system as claimed in claim 2, wherein said means for conveying gas between each test cell and counting means includes an in-line filter for removing undesirable elements from the circulating test gas.

11. A method of testing a test sample for gas diffusion characteristics, comprising the steps of:
    providing a test chamber;
    providing a test cell within said test chamber and with an opening;
    mounting a test sample over said opening so that gas molecules not previously present in said test cell can only enter said test cell by diffusing across said test sample;
    charging said test chamber to a pressure greater than atmospheric; and
    determining the concentration of test gas that diffuses across said test sample into said test cell.

12. An apparatus for testing material samples comprising a sealed test chamber enclosing a plurality of test cells, each test cell having an open end for sealingly mounting a test sample, a means for indicating the amount of diffusion across each of said test samples, a means to determine the relative pressure between said test cells and said test chamber, and a means to connect a test gas source to said test gas chamber.

13. The apparatus of claim 12, wherein said test chamber comprises a removable top.

14. The apparatus of claim 12, wherein each of said test cells is provided with three ports, namely, a supply port, a return port and a pressure sensing port, and said means to determine the relative pressure between said test cells and said test chamber is connected to said pressure sensing port, and said means for indicating the amount of diffusion across said test samples is connected to said supply port and said return port.

15. The apparatus of claim 14, wherein said means for indicating the amount of diffusion across said test samples is adapted to indicate the amount of radon gas that has diffused across said test sample.

* * * * *